United States Patent
McCarthy et al.

(10) Patent No.: US 7,425,214 B1
(45) Date of Patent: Sep. 16, 2008

(54) HIP ARTHROPLASTY TRIALING APPARATUS WITH ADJUSTABLE PROXIMAL TRIAL AND METHOD

(75) Inventors: Thomas F. McCarthy, Neshanic Station, NJ (US); Christopher DeMaria, Glen Rock, NJ (US); Jason R. Cahayla, Wanaque, NJ (US)

(73) Assignee: Howmedica Osteonics Corp., Mahwah, NJ (US)

( * ) Notice: Subject to any disclaimer, the term of this patent is extended or adjusted under 35 U.S.C. 154(b) by 55 days.

(21) Appl. No.: 11/071,793

(22) Filed: Mar. 3, 2005

(51) Int. Cl.
*A61B 17/74* (2006.01)
(52) U.S. Cl. ...................................................... 606/89
(58) Field of Classification Search .................. 606/89, 606/91, 102
See application file for complete search history.

(56) References Cited

U.S. PATENT DOCUMENTS

| | | | |
|---|---|---|---|
| 5,314,479 A * | 5/1994 | Rockwood et al. ....... | 623/19.14 |
| 5,336,268 A | 8/1994 | Rispeter | |
| 5,569,263 A * | 10/1996 | Hein ........................... | 606/102 |
| 5,800,554 A * | 9/1998 | Scholz ..................... | 623/22.43 |
| 5,860,982 A | 1/1999 | Ro et al. | |
| 6,083,263 A | 7/2000 | Draenert et al. | |
| 6,136,036 A | 10/2000 | Scholz | |
| 2004/0054419 A1 | 3/2004 | Serra et al. | |
| 2004/0122440 A1* | 6/2004 | Daniels et al. .............. | 606/102 |
| 2005/0049601 A1* | 3/2005 | Keller .......................... | 606/81 |

* cited by examiner

*Primary Examiner*—Eduardo C. Robert
*Assistant Examiner*—Jerry Cumberledge
(74) *Attorney, Agent, or Firm*—Arthur Jacob

(57) ABSTRACT

Apparatus and method are described for interoperatively determining, during a trailing procedure conducted in connection with total hip arthroplasty, a combination of neck length and femoral head offset required in a femoral component for establishing appropriate hip mechanics in a prosthetic hip joint to be implanted at an implant site. A trial femoral head is coupled for selective movement relative to a femoral stem component to move the trial femoral head longitudinally and laterally relative to a predetermined direction among selected combinations of trial distance and trial offset to evaluate hip mechanics and determine interoperatively an appropriate combination of trial distance and trial offset corresponding to the combination of neck length and femoral head offset required in the prosthetic hip joint.

8 Claims, 10 Drawing Sheets

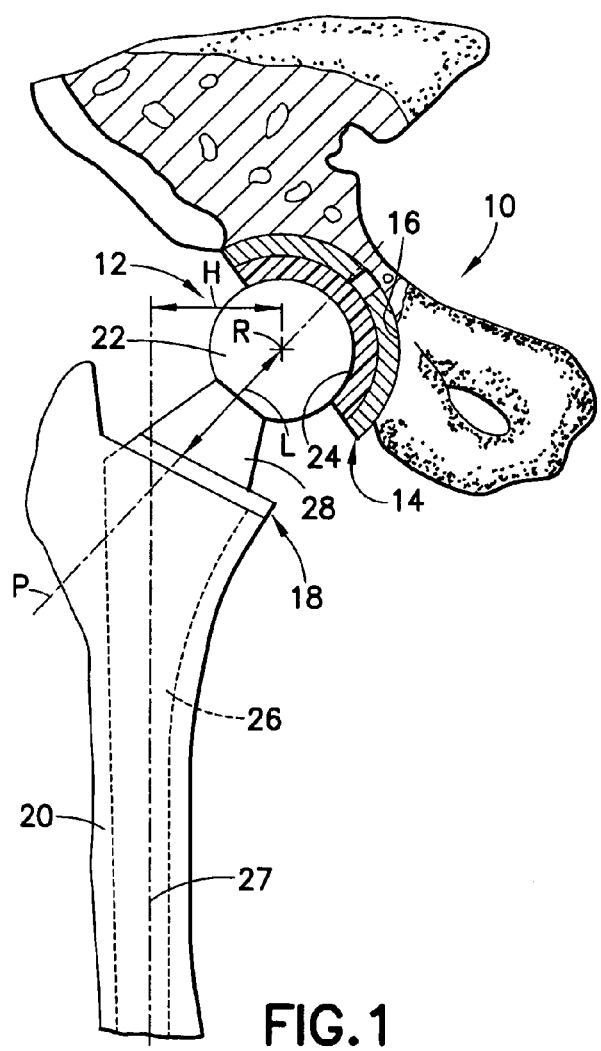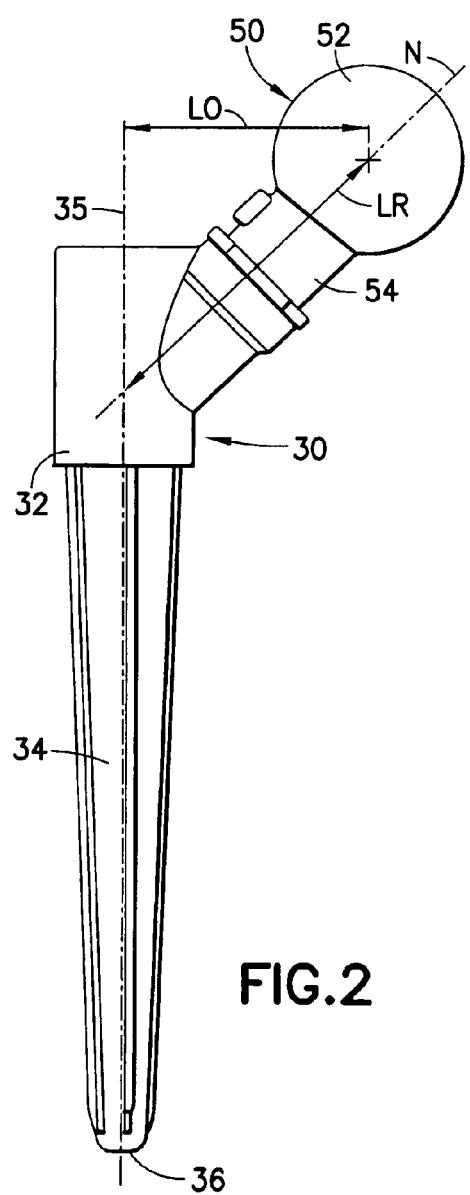
FIG.1
FIG.2

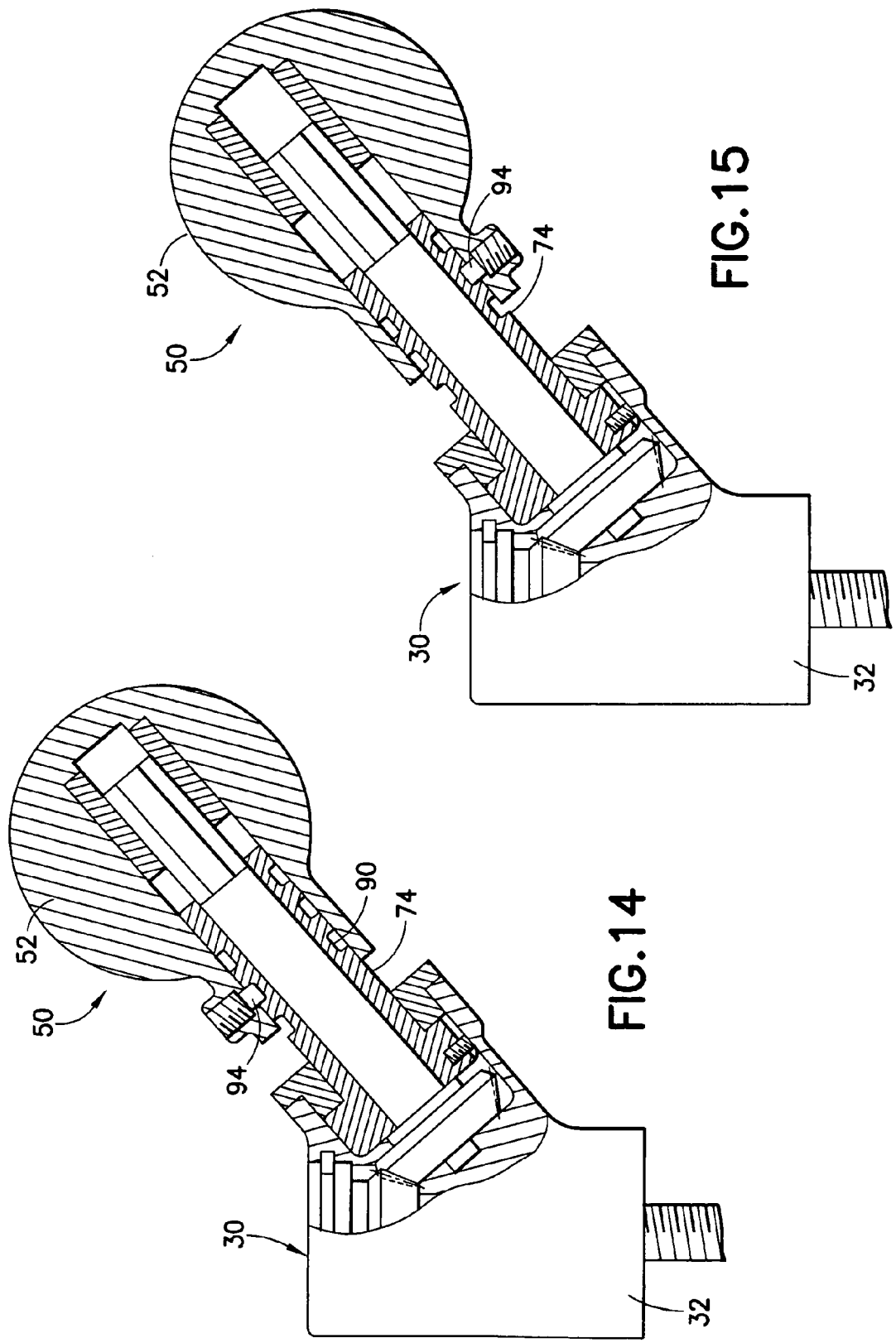

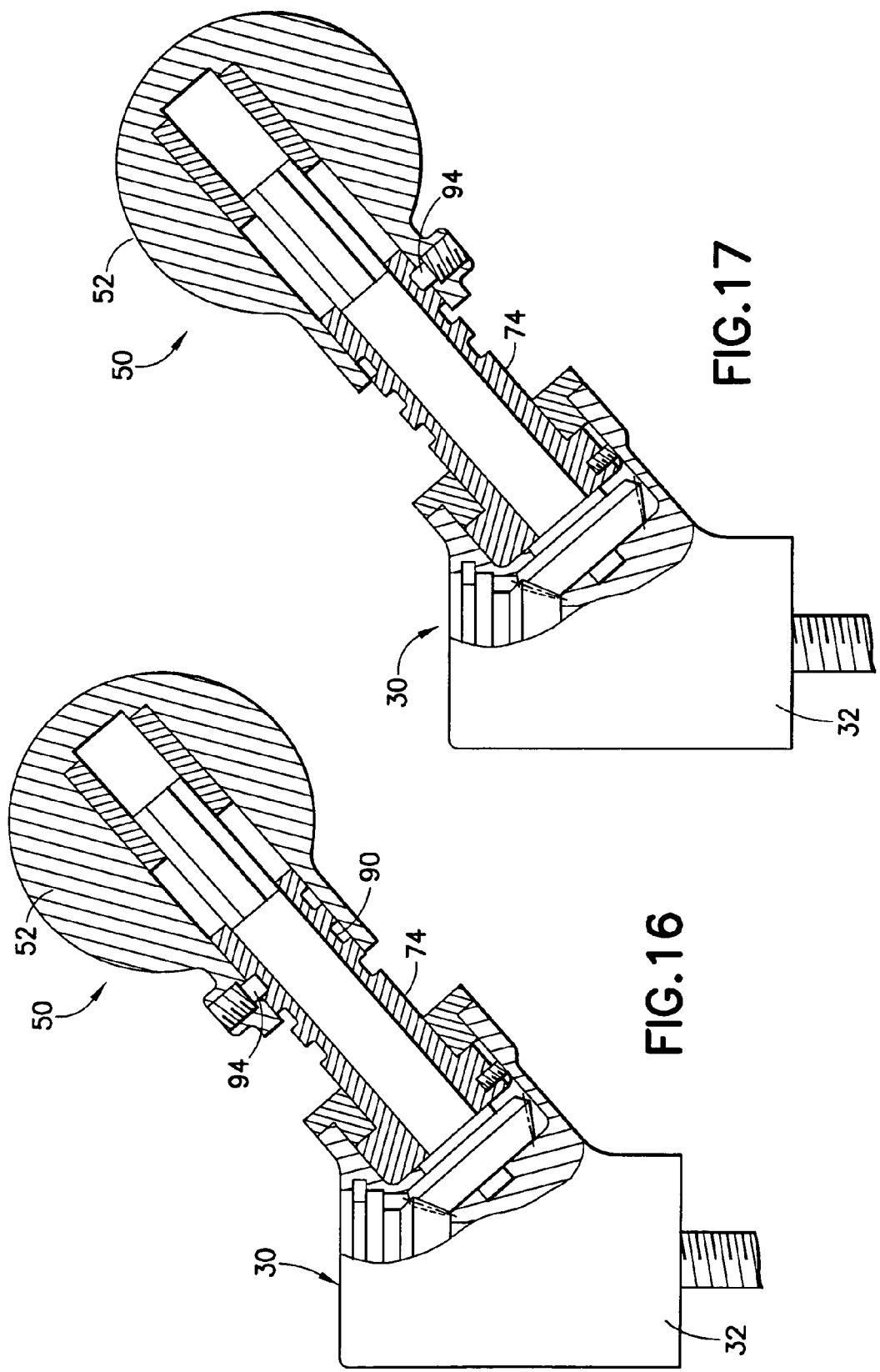

HIP ARTHROPLASTY TRIALING APPARATUS WITH ADJUSTABLE PROXIMAL TRIAL AND METHOD

BACKGROUND OF THE INVENTION

1. Field of the Invention

The present invention relates generally to hip arthroplasty and pertains, more specifically, to apparatus and method for conducting interoperative trailing to determine an appropriate neck length and head offset in the femoral component of a prosthetic hip joint.

2. Description of Related Art

Total hip arthroplasty requires the preparation of an implant site for the reception of a femoral component and an acetabular component of a prosthetic hip joint to be implanted at the implant site. Proper hip mechanics are achieved through the selection of an appropriate neck length and head offset in the femoral component of the prosthetic hip implant. That is, the distance between the stem of the femoral component and the femoral head of the component, provided by the length of the neck along a predetermined direction of the neck, and the lateral offset between the stem of the femoral component and the femoral head, establishes the requisite neck length and head offset which, in turn, provides the desired range of motion, leg length, and tension in the soft tissue at the implant site. Accordingly, of utmost importance is the ability to determine the appropriate neck length and head offset with precision, and to do so with ease and assurance.

A determination of the appropriate length required for the neck of a femoral component and the appropriate head offset is conducted once the size of each of the femoral component and the acetubular component is selected, and the implant site is prepared for the reception of each selected component. A preliminary assessment can be made utilizing radiographic analysis; however, a final determination usually is accomplished during the course of the implant procedure itself, that is, interoperatively.

In a current trailing procedure, serial trial prostheses are used to determine the appropriate neck length and head offset during the conduct of total hip arthroplasty. Thus, the hip joint is dislocated, a provisional trial prosthesis is put into place, the hip joint is reduced, and the leg of the patient is moved by a surgeon through a range of motion to determine hip mechanics, by hand. The trailing procedure requires that the trial prosthesis be removed and replaced with another in a series of trial prostheses in order to evaluate the effect of different neck lengths and head offsets on hip mechanics. To achieve correct hip mechanics, a surgeon may need to perform several iterations, each requiring replacement of one trial prosthesis with another in the series, reduction of the hip joint, movement through a range of motion, and then dislocation of the joint again in order to change trials. The procedure can be quite time-consuming and even physically challenging, especially with larger patients. Moreover, the procedure is not suited to the conduct of more recently developed minimally invasive total hip arthroplasty where access to the hip joint is more limited.

BRIEF SUMMARY OF THE INVENTION

The present invention provides apparatus and method by which the appropriate neck length and head offset in a femoral component of a prosthetic hip joint is determined interoperatively with ease and with accuracy, for accomplishing optimal hip mechanics. As such, the present invention attains several objects and advantages, some of which are summarized as follows: Facilitates an interoperative determination of the appropriate neck length and head offset for a femoral component in a total hip arthroplasty; enables relatively quick and effective interoperative trialing for evaluation of hip mechanics at a prosthetic hip implant site; allows selective changes in distance and offset between the femoral stem and a trial femoral head of a femoral trial in a prosthetic hip joint for interoperatively determining an appropriate neck length and head offset in the femoral component of the prosthetic hip joint itself, without the necessity for serial replacements of the entire trial and concomitant multiple dislocations and reductions of the hip joint; allows such selective changes in distance and offset to be accomplished with a single apparatus, utilizing a single operator coupled readily to the apparatus and capable of operation from a location remote from the implant site; provides for the ready replication of any one of a plurality of predetermined combinations of neck length and head offset available in a given hip replacement system to enable selection of the combination most appropriate to a particular implant site; enables interoperative evaluation of hip mechanics at a hip implant site for consistent, precise results attained with ease and in less time; improves accuracy in the completion of a total hip arthroplasty; facilitates the conduct of minimally invasive total hip arthroplasty, where access to the hip joint is more limited; reduces pain and discomfort, as well as recovery time, in patients subjected to total hip arthroplasty.

The above objects and advantages, as well as further objects and advantages, are attained by the present invention which may be described briefly as apparatus for interoperatively determining, during a trialing procedure conducted in connection with total hip arthroplasty at an implant site, a combination of neck length and femoral head offset required in a femoral component to be engaged with an acetabular component in a prosthetic hip joint to be implanted at the implant site for establishing appropriate hip mechanics in the prosthetic hip joint, by selecting a combination of trial distance, along a predetermined direction, and trial offset between a trial femoral head and a femoral stem component placed at the implant site with the trial femoral head engaged with an acetabular component in a trial hip joint, the combination of trial distance and trial offset corresponding to the combination of neck length and femoral head offset required in the prosthetic hip joint, the apparatus comprising: a trial femoral head component including a trial femoral head having a center of rotation; an indexing arrangement coupling the trial femoral head component with the femoral stem component for selective movement relative to one another, during the trialing procedure, the movement including longitudinal movement of the femoral head along the predetermined direction and lateral movement of the femoral head relative to the predetermined direction for establishing a trial hip joint having a selected combination of trial distance and trial offset between the trial femoral head and the femoral stem component; and a drive mechanism for selectively driving the indexing arrangement to index the trial femoral head component among selected combinations of trial distance and trial offset, during interoperative trialing to evaluate hip mechanics in the trial hip joint, thereby determining interoperatively an appropriate combination of trial distance and trial offset; the appropriate combination of trial distance and trial offset corresponding to the combination of neck length and femoral head offset required in the femoral component for establishing the appropriate hip mechanics in the prosthetic hip joint.

In addition, the present invention provides a method for interoperatively determining, during a trialing procedure conducted in connection with total hip arthroplasty at an implant site, a combination of neck length and femoral head offset required in a femoral component to be engaged with an acetabular component in a prosthetic hip joint to be implanted at the implant site for establishing appropriate hip mechanics in the prosthetic hip joint, by selecting a combination of trial distance, along a predetermined direction, and trial offset between a trial femoral head of a trial femoral head component and a femoral stem component placed at the implant site with the trial femoral head engaged with an acetabular component in a trial hip joint, the combination of trial distance and trial offset corresponding to the combination of neck length and femoral head offset required in the prosthetic hip joint, the method comprising: coupling the trial femoral head with the femoral stem component for selective movement relative to one another, during the trialing procedure, the movement including movement of the trial femoral head longitudinally along the predetermined direction and laterally relative to the predetermined direction for establishing a trial hip joint having a selected combination of trial distance and trial offset between the trial femoral head and the femoral stem component; and selectively moving the trial femoral head longitudinally and laterally relative to the predetermined direction among selectable combinations of trial distance and trial offset, during interoperative trialing to evaluate hip mechanics in the trial hip joint, thereby determining interoperatively an appropriate combination of trial distance and trial offset, the appropriate combination of trial distance and trial offset corresponding to the combination of neck length and the femoral head offset required in the femoral component for establishing the appropriate hip mechanics in the prosthetic hip joint.

BRIEF DESCRIPTION OF THE SEVERAL VIEWS OF THE DRAWING

The invention will be understood more fully, while still further objects and advantages will become apparent, in the following detailed description of preferred embodiments of the invention illustrated in the accompanying drawing, in which:

FIG. 1 is a pictorial illustration, somewhat diagrammatic, of a prosthetic hip joint implanted at an implant site;

FIG. 2 is a side elevational view of apparatus constructed in accordance with the present invention;

FIGS. 12 through 17 are fragmentary cross-sectional views, similar to FIG. 6, and showing component parts of the apparatus in different selectable indexed positions.

DETAILED DESCRIPTION OF THE INVENTION

Figure 3:
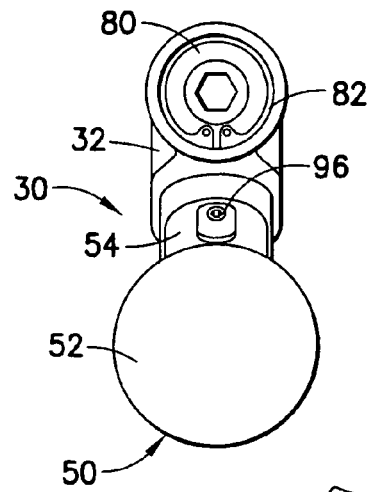
FIG. 3 is a top plan view of the apparatus.
Figure 5:
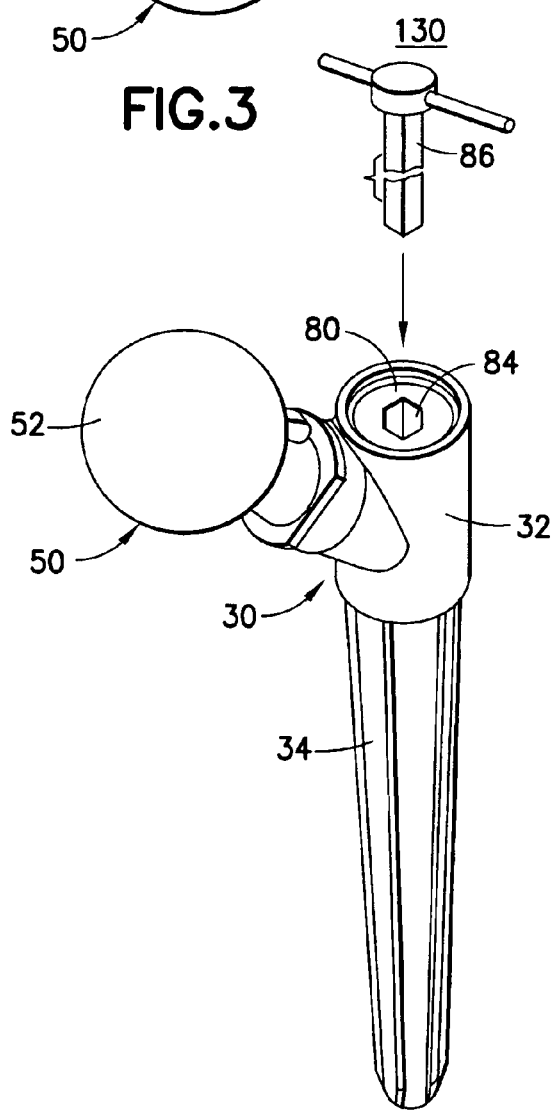
FIG. 5 is a top front perspective view of the apparatus.
Figure 4:
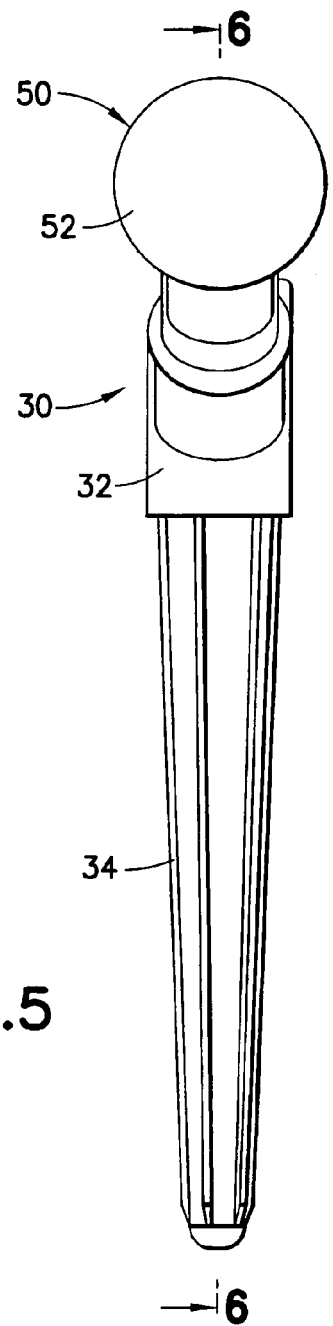
FIG. 4 is a front elevational view of the apparatus.

Referring now to the drawing, and especially to FIG. 1 thereof, an implant site 10 has been provided with a prosthetic hip joint 12 which is seen to include an acetabular component 14 implanted in acetabulum 16, and a femoral component 18 implanted in proximal femur 20. Femoral component 18 includes a femoral head 22, which is engaged with a bearing surface 24 of the acetabular component 14 for articulation of the prosthetic hip joint 12, a femoral stem 26, which extends along a longitudinal axis 27 and is affixed within the proximal femur 20 to secure the femoral component 18 in place, and a femoral neck 28, which connects the femoral head 22 to the femoral stem 26 and which spaces the femoral head 22 from the femoral stem 26, all as now well-known in prosthetic hip joints.

As is conventional, prosthetic hip joint 12 relies upon soft tissue (not shown) at the implant site 10 to maintain femoral head 22 of femoral component 18 appropriately engaged with bearing surface 24 of acetabular component 14 for proper hip mechanics at the hip joint 12. The attainment of requisite appropriate hip mechanics, including range of motion, leg length and tension in the soft tissue, is dependent upon the distance between the femoral head 22 and the femoral stem 26 provided by the femoral neck 28, as represented by the length L which extends along a predetermined direction P between the center of rotation R of femoral head 22 and the femoral stem 26, and upon head offset, as represented by the lateral offset H between the center of rotation R of femoral head 22 and axis 27 of femoral stem 26. The desired hip mechanics are attained by selecting an appropriate length L and an appropriate offset H. Accordingly, in order optimize hip mechanics, length L and offset H must be selected with precision.

Figure 8:
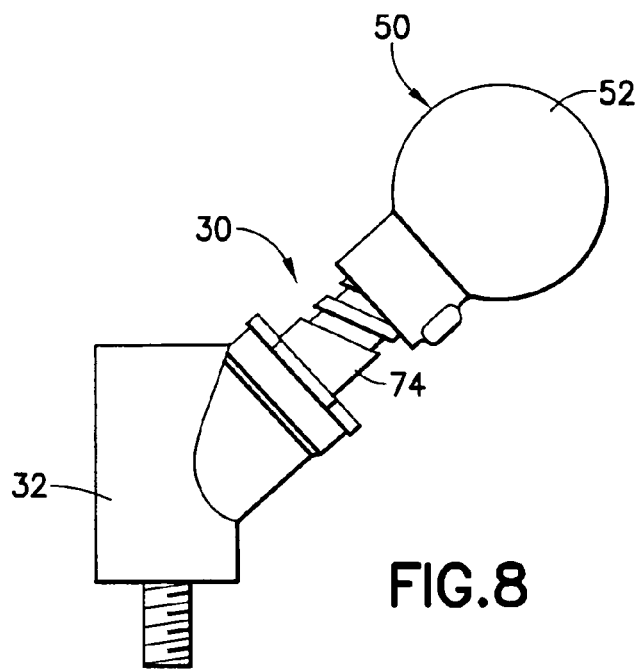
FIG. 8 is a side elevational view of a portion of the apparatus, similar to FIG. 2, but showing component parts in another operating position.
Figure 9:
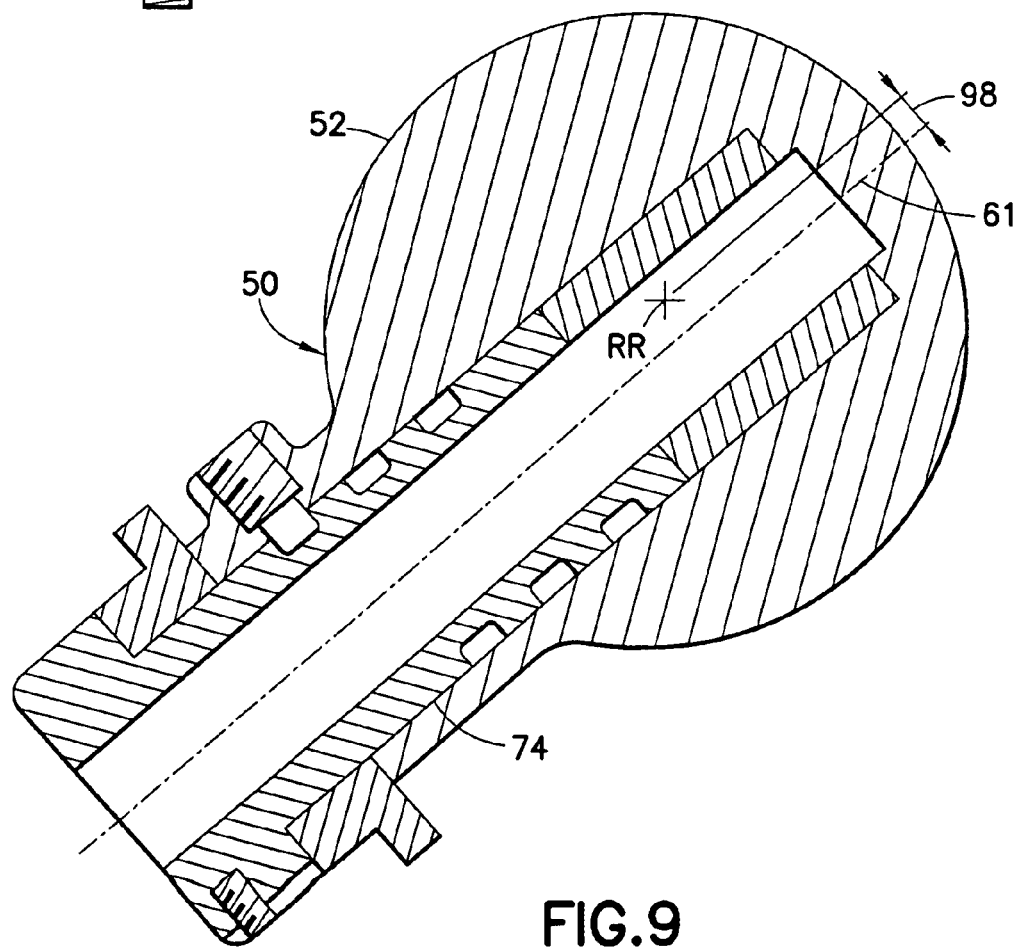
FIG. 9 is a largely diagrammatic illustration of a portion of the apparatus.

Turning now to FIGS. 8 through 9, an apparatus constructed in accordance with the present invention is illustrated at 30 and is seen to include a proximal housing 32 shown seated upon a femoral stem 34. Femoral stem 34 extends along a longitudinal axis 35 between a distal end 36 and a proximal end 38. A tapered post 40 at the proximal end 38 of the femoral stem 34 is shown received within a complementary tapered recess 42 in housing 32 to mount the housing 32 in a fixed position upon the femoral stem 34. A bolt 44 is threaded into femoral stem 34 and secures the housing 32 in place at the fixed position at proximal end 38.

Figure 6:
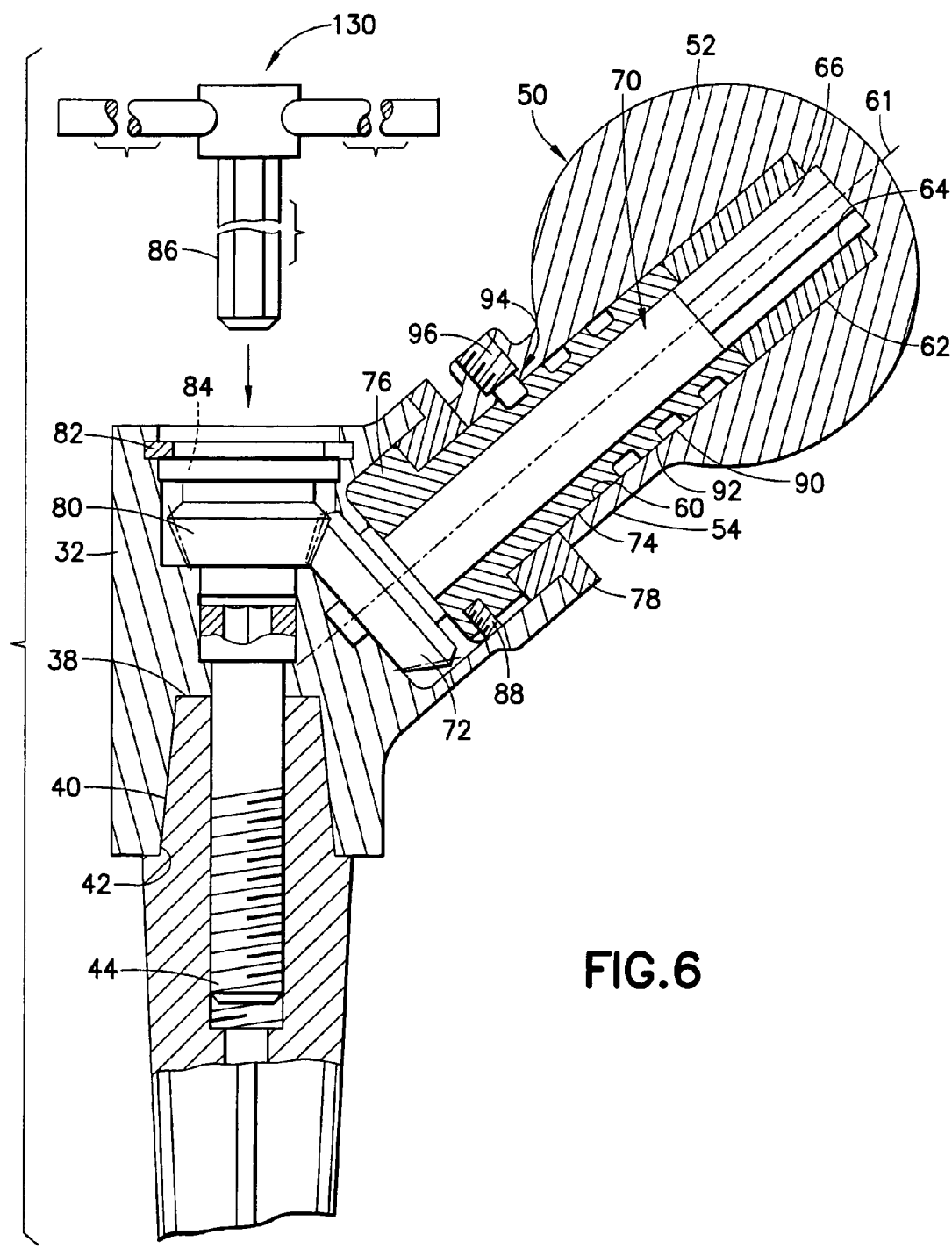
FIG. 6 is an enlarged, fragmentary cross-sectional view taken along line 6-6 of FIG. 4.
Figure 7:
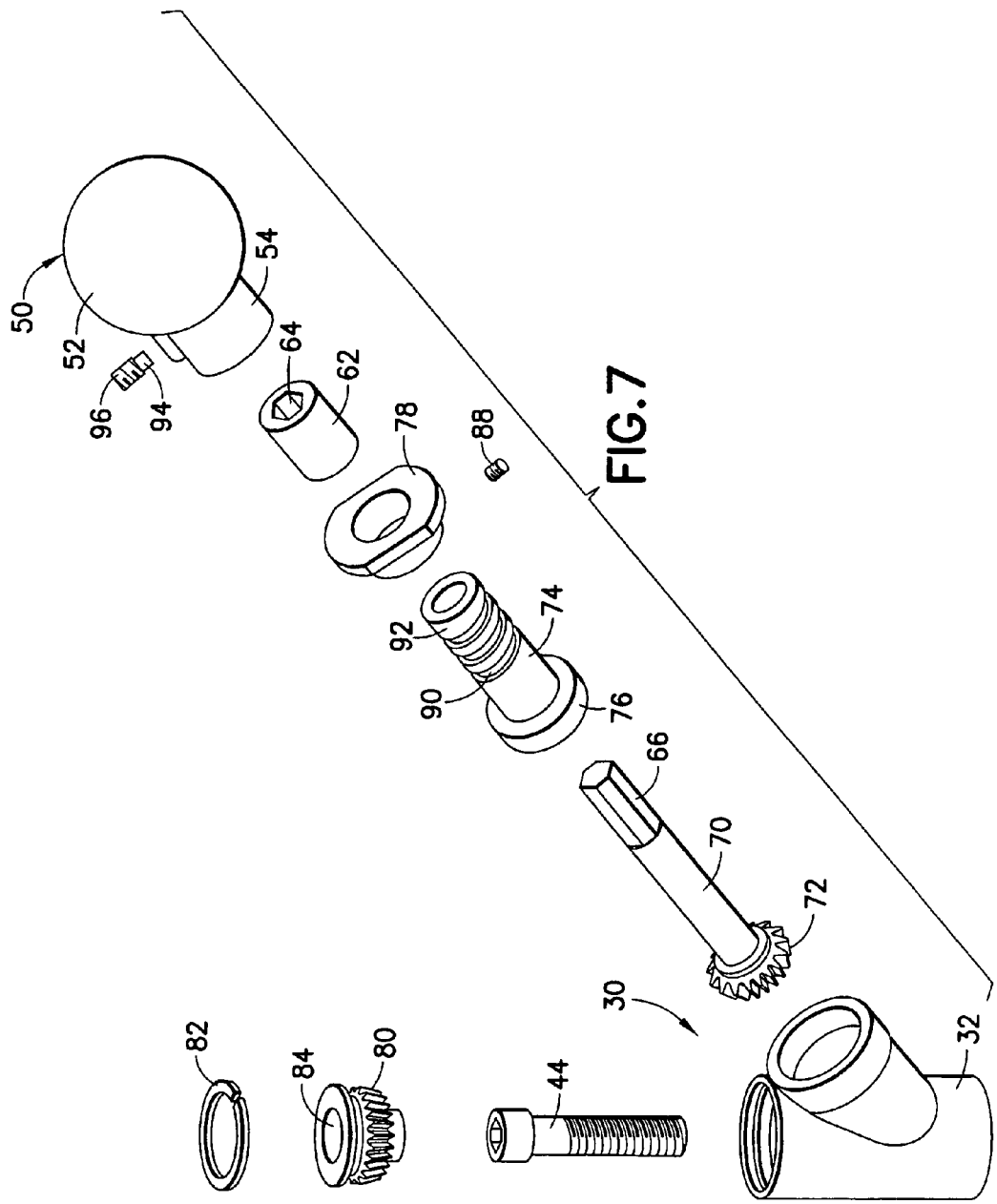
FIG. 7 is an exploded perspective view of the apparatus.

A trial femoral head component 50 is carried by the housing 32 and includes a generally spherical head 52 having a center of rotation RR spaced from the femoral stem 34 a distance LR along a predetermined direction N, and offset laterally from axis 35, as illustrated by lateral offset LO. A collar 54 is unitary with spherical head 52 and is shown positioned adjacent housing 32, between the housing 32 and head 52. As best seen in FIG. 6, trial femoral head component 50 includes a bore 60 extending along an axis of rotation 61, generally parallel with the predetermined direction N, and an insert 62 is seated within bore 60, affixed to head portion 52, as by an interference fit, so as to be integrated with femoral head component 50 for movement with femoral head component 50. Insert 62 includes a central, axial passage 64 having a hexagonal cross-sectional configuration, as seen in FIG. 7, and engages an end portion 66 of a drive shaft 70 journaled for rotation within housing 32, about axis 61, which serves as a drive axis. End portion 66 has a hexagonal cross-sectional configuration complementary to the hexagonal cross-sectional configuration of axial passage 64 of insert 62 so that insert 62, and consequently femoral head component 50, are coupled with the drive mechanism which includes drive shaft 70 for rotation with the drive shaft 70, while allowing sliding movement of the insert 62, and femoral head component 50, axially along the drive shaft 70.

Drive shaft 70 carries a pinion gear 72 journaled for rotation within housing 32 and extends through a sleeve 74 having a base 76 seated within housing 32 and affixed in place by a retainer 78. A drive pinion 80 is journaled for rotation within housing 32 and is captured within housing 32 by a clip 82 which maintains drive pinion 80 engaged with pinion gear 72. A hexagonal drive socket 84 in drive pinion 80 is accessible for engagement by a complementary wrenching tool 86, for purposes to be described in detail hereinafter. Suffice it to say, at this juncture, that rotation of drive pinion 82 will rotate drive shaft 70 about axis of rotation 61, which results in rotation of trial femoral head component 50 about axis 61, while rotation of sleeve 74 about axis 61, within housing 32, is precluded by a pin 88. Drive socket 84 passes axially entirely through drive pinion 80 so as to provide access to bolt 44 for ready attachment of the housing 32 to the stem 34, and for selective detachment of the housing 32 from the stem 34.

Sleeve 74 carries a lead groove 90 which follows a path around generally cylindrical outer surface 92 of sleeve 74. A follower 94 in the form of a threaded pin 96 extends through the collar 54 of the trial femoral head component 50 and is engaged within the lead groove 90 such that upon rotation of the drive shaft 70, and concomitant rotation of the trial femoral head component 50, about axis of rotation 61, trial femoral head component 50 will be translated axially along axis 61, between a lowermost position, as seen in FIGS. 2 through 6, and an uppermost position, as shown in FIG. 8, enabling a selective adjustment of the distance LR between the center of rotation RR of the spherical head 52 and the femoral stem 34 along the axis of rotation 61. As shown diagrammatically in FIG. 9, the center of rotation RR of the spherical head 52 is offset laterally from the axis of rotation 61, as illustrated by offset 98, so that rotation of the trial femoral head component 50 about axis 61 also effects selective changes in the lateral offset LO of the spherical head 52, all as will be described in greater detail below.

Figure 10:
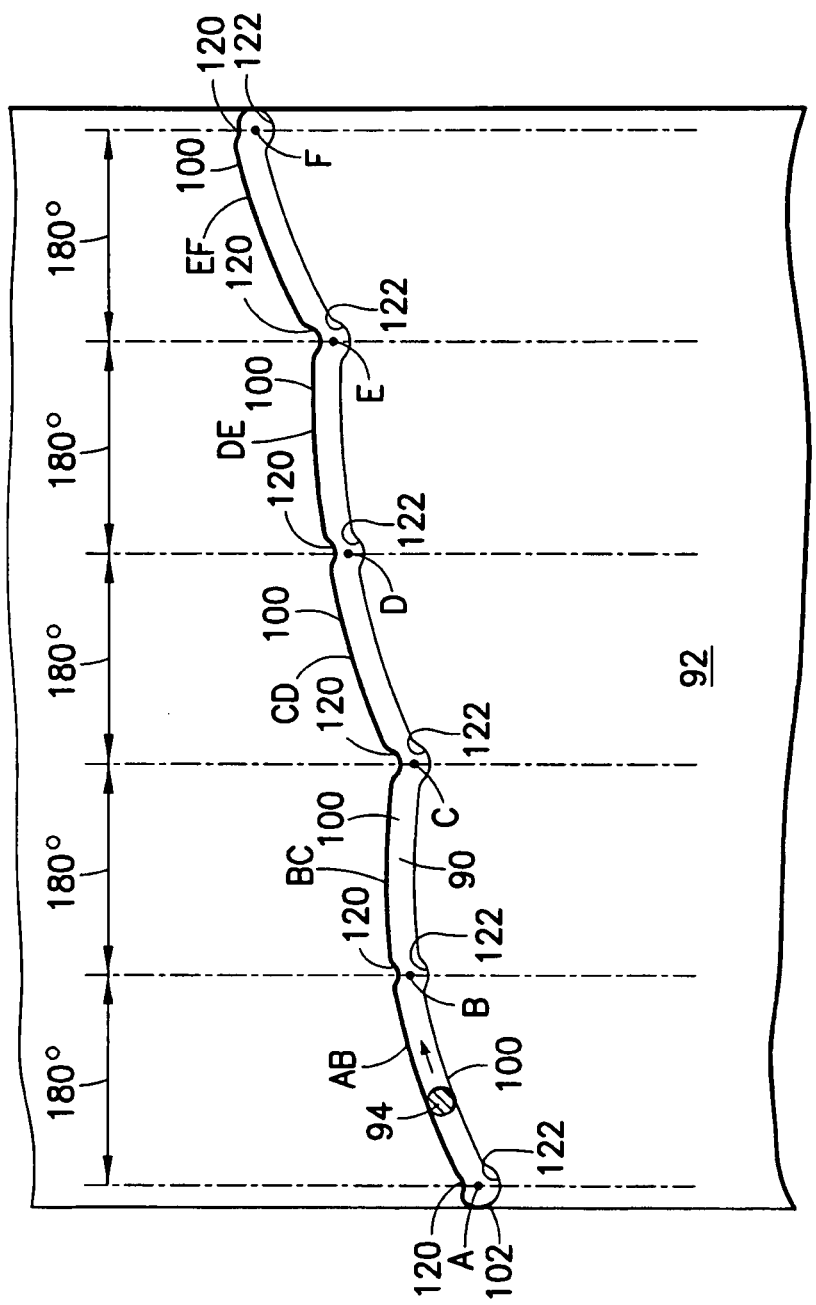
FIG. 10 is a diagrammatic illustration in the form of a planar projection of a cylindrical surface of a component part of the apparatus and demonstrating the operation of the apparatus.

Referring now to FIGS. 10 through 17, as well as to FIGS. 2 through 9, lead groove 90 follows a modified helical path and includes a plurality of segments 100 located serially along the lead groove 90, as shown diagrammatically in FIG. 10. The segments 100 are oriented and configured for selective movement of trial femoral head component 50 to index the trial femoral head component 50 among selectable combinations of trial distance and trial offset, in response to rotation of drive shaft 70. Thus, at the lowermost position of trial femoral head component 50, follower 94 is located at end 102 of lead groove 90, the position of the trial femoral head component 50 and the follower 94 being depicted in FIGS. 10 and 11 by position A, and center of rotation RR of spherical head 52 is placed at distance LR and lateral offset LO, thereby locating spherical head 52 at a first predetermined combination of trial distance and trial offset. The lowermost position of femoral head component 50 is illustrated in greater detail in FIG. 12.

Figure 11:
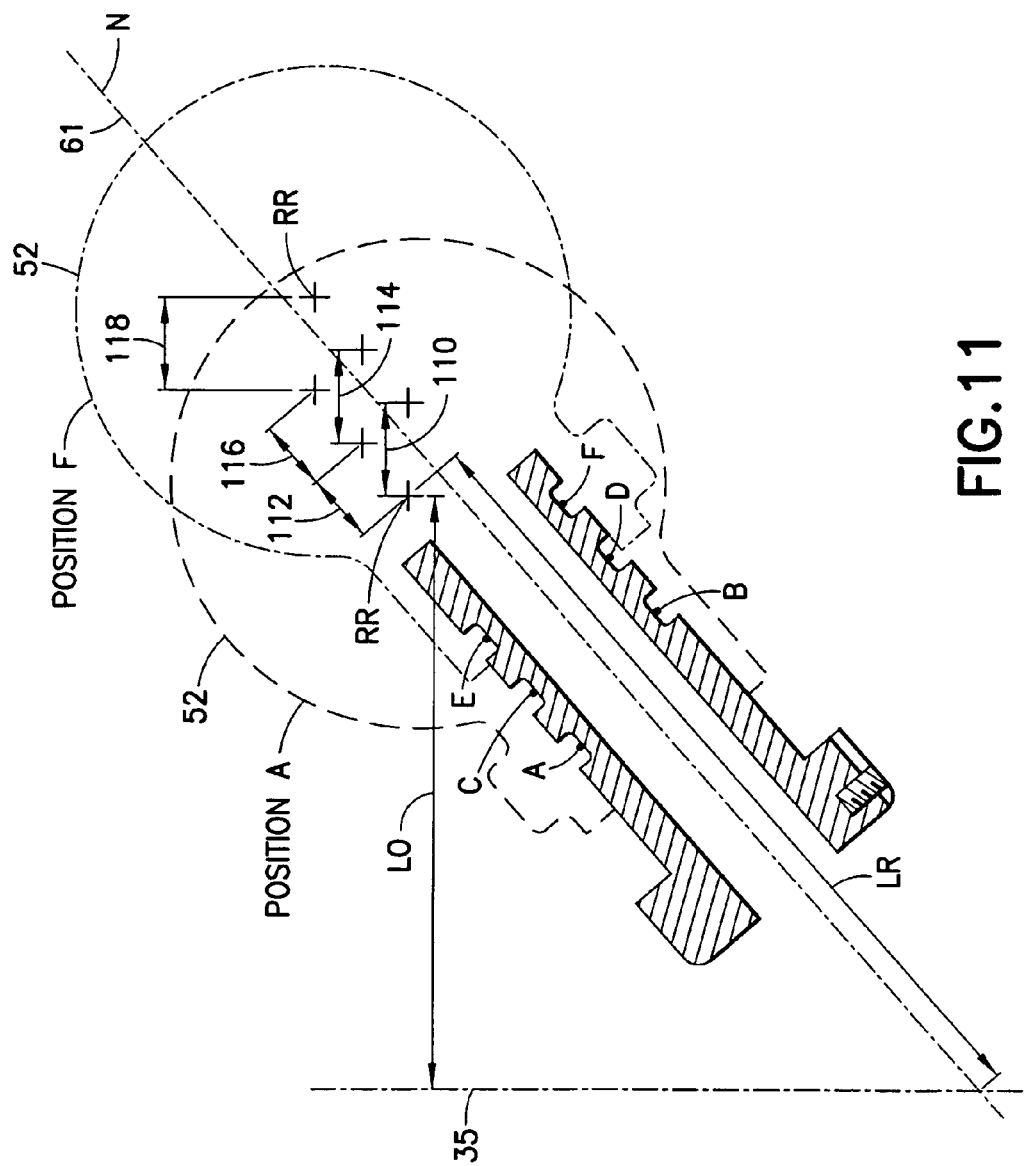
FIG. 11 is a diagrammatic illustration showing various selectable positions of component parts of the apparatus.
Figure 13:
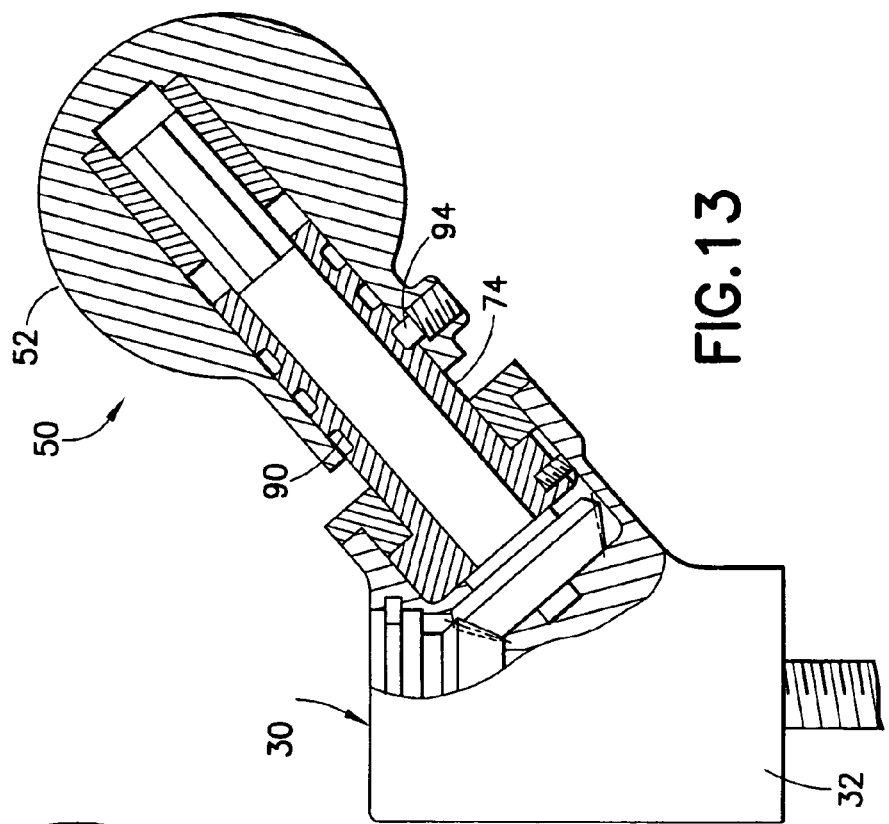
Figure 12:
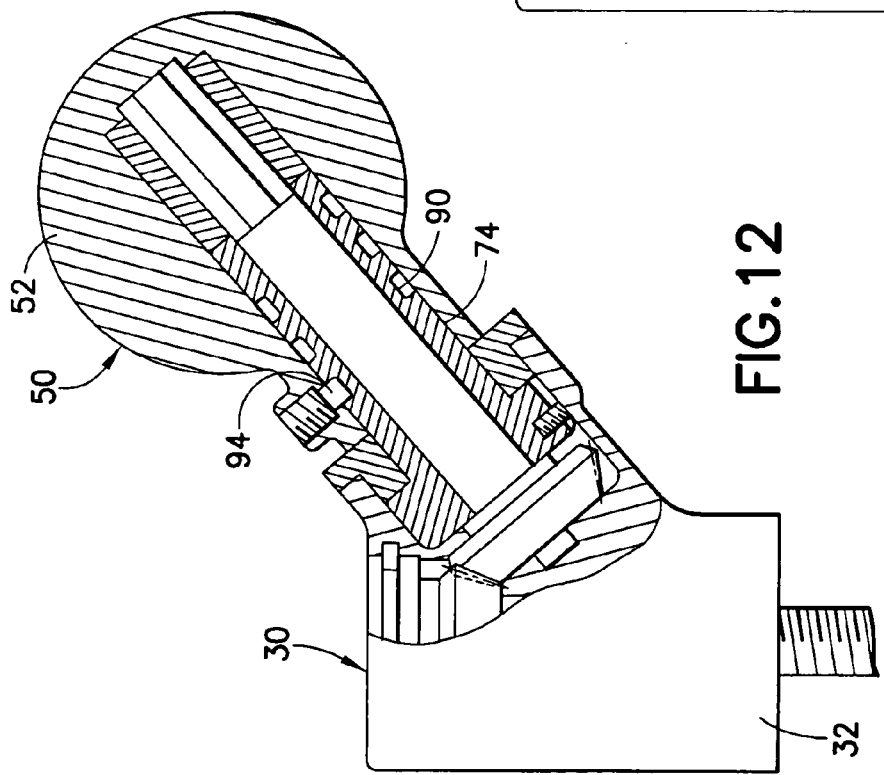

Upon an initial selective rotation of drive shaft 70, and concomitant rotation of trial femoral head component 50,, through 180° of rotation about axis 61, segment AB of lead groove 90 is traversed by follower 94, and trial femoral head component 50 and follower 94 move from position A to position B. As a result of the offset 98 between axis 61 and the center of rotation RR of the spherical head 52, such rotation through 180° effects a change in the lateral offset LO of the spherical head 52, as represented in FIG. 11 by the increment 110 of lateral distance between positions of the center of rotation RR corresponding to positions A and B of the follower 94 and trial femoral head component 50. Hence, for the trial distance along predetermined direction N, represented by position A, spherical head 52 of trial femoral head component 50 is provided with either one of first and second selectable predetermined combinations of trial distance and trial offset, represented by positions A and B. The position of the trial femoral head component 50 corresponding to position B is illustrated in greater detail in FIG. 13.

Further selective rotation of drive shaft 70 through a subsequent 180° of rotation will move follower 94 along next consecutive segment BC of lead groove 90, thereby effecting movement of spherical head 52 of trial femoral head component 50 to position C where the trial distance LR between the center of rotation RR of the spherical head 52 and the femoral stem 34 is increased over that at position A by an increment 112 of distance along the predetermined direction N and spherical head 52 is placed at a third predetermined combination of trial distance and trial offset, depicted in detail in FIG. 14. Continued rotation of drive shaft 70 through another 180° of rotation will move follower 94 along next consecutive segment CD of lead groove 90, thereby changing the lateral offset of the spherical head 52 by an increment 114 of lateral distance between positions of center of rotation RR corresponding to positions C and D and placing the trial femoral head component 50 in the position shown in FIG. 15. Thus, for the trial distance represented by position C, spherical head 52 of trial femoral head component 50 is provided with either one of third and fourth selectable predetermined combinations of trial distance and trial offset, represented by positions C and D.

Still further selective rotation of drive shaft 70 through a subsequent 180° of rotation will move follower 94 along next consecutive segment DE of lead groove 90, thereby effecting movement of spherical head 52 of trial femoral head component 50 to position E where the distance LR between the center of rotation RR of the spherical head 52 and the femoral stem 34 is increased over that at position C by an increment 116 of distance along the predetermined direction N and spherical head 52 is placed at a fifth predetermined combination of trial distance and trial offset, shown in FIG. 16. Continued rotation of drive shaft 70 through another 180° of rotation will move follower 94 along next consecutive segment EF of lead groove 90, thereby changing the lateral offset LO of the spherical head 52 by an increment 118 of lateral distance between positions E and F and placing trial femoral head component 50 in the position depicted in FIG. 17. Thus, for the trial distance represented by position E, spherical head 52 of trial femoral head component 50 is provided with either one of fifth and sixth selectable predetermined combinations of trial distance and trial offset, represented by positions E and F.

A detent 120 is placed at each terminal end of the segments AB, BC, CD, DE and EF, each detent 120 being in the form of a notch 122 generally complementary to pin 96 and communicating with lead groove 90 so that a positive stop is established for follower 94 at each position A, B, C, D, E and F. Follower 94 is captured at each detent 120 so that the detents 120 serve as an indicator for indicating placement of the trial femoral head component 50 at a selected position and placement of spherical head 52 at a corresponding selectable predetermined combination of trial distance and trial offset. In addition, the detents 120 assure that the trial femoral head component 50 is retained at a selected position during trialing to determine hip mechanics. The retention force of a detent 120 is overcome readily for selective movement of the trial femoral head component 50 from one position to another.

As described above, the arrangement for indexing trial femoral head component 50 provides trialing apparatus 30 with six optional combinations of trial distance and trial offset of spherical head 52 in a single trialing apparatus, representing six combinations of neck length and head offset conventionally made available to a surgeon in an instrument set of trials for a femoral component of a given size. For example, by setting increments 110, 114 and 118 of lateral distance at 5 mm, and setting increments 112 and 116 of longitudinal distance at 4 mm, the single trialing apparatus 30 is capable of replicating six different predetermined combinations of trial distance and trial offset and can replace six individual trials of a typical conventional set of trial instruments ordinarily utilized to determine optimum neck length and head offset required in a femoral component of selected size. Thus, once having determined the size of a femoral component to be implanted at a particular implant site, a surgeon can utilize the single trialing apparatus 30 to determine which combination of neck length and femoral head offset is required in a femoral component for establishing the appropriate hip mechanics in the prosthetic hip joint to be implanted at the implant site. Once a proximal femur is prepared for the reception of a femoral component of appropriate size, femoral stem 34 is put into place in the proximal femur. Femoral stem 34 may be in the form of a trial femoral stem, or may be a modular femoral stem of a modular femoral component of the complete prosthetic hip joint itself. In either case, housing 32 of trialing apparatus 30 is installed at the proximal end 38 of the femoral stem 34, and is selectively removed from stem 34, as described above.

Once bolted to the proximal end 38 of the femoral stem 34, trialing apparatus 30 selectively is adjusted, interoperatively, among the several combinations of trial distance and trial offset available, as described above, enabling an evaluation of hip mechanics for each combination without the necessity for removing and replacing a trialing component for each combination, and without concomitant multiple dislocations and reductions of the hip joint during trialing, as may be required with conventional trialing instruments sets wherein a separate trialing component is provided for each combination of trial distance and trial offset. A surgeon need merely insert a wrenching tool 86 into the drive socket 84 of the drive pinion 80 to drive the drive pinion 80, preferably from a remote location 130, to adjust trialing apparatus 30 to any one of the six predetermined combinations of trial distance and trial offset.

As described above, the detents 120 at the respective terminal ends of the segments 100 of the lead groove 90 provide the surgeon with an indication of the placement of the trial femoral head component 50 at a position A, B, C, D, E or F and retains the trial femoral head component 50 in a selection position A, B, C, D, E or F during evaluation of the hip mechanics provided by the combination of trial distance and trial offset made available at the selected position. Furthermore, a surgeon may choose to visit any of the available positions in any sequence and for any number of repeated visits for refining the evaluation of hip mechanics without the necessity for a corresponding number of dislocations and reductions of the hip joint. Upon reaching a position where appropriate hip mechanics are attained, trial distance and trial offset are recorded, and trialing apparatus 30 is removed and replaced by a femoral component having the corresponding required neck length and head offset, as determined by the trialing procedure.

It is noted that trialing apparatus 30 is well-suited to the utilization of minimally invasive surgical techniques in that the trial femoral head component 50 of the trialing apparatus 30 can be retracted to the lowermost position, as illustrated in FIGS. 2 through 6, placing the trialing apparatus 30 in a most compact configuration for both insertion and removal, thereby minimizing the size of an incision required at the implant site. In addition, the ability to operate trialing apparatus 30 from a remote location 130, through the use of a remotely operated wrenching tool 86, facilitates selective movement of the trial femoral head component 50 among the several positions which provide the several combinations of trial distance and trial offset, for a minimally invasive trialing procedure.

The simplified construction of apparatus 30, comprising a limited number of readily assembled component parts, enables ease of maintenance and cleaning, as well as operation, for exemplary performance over an extended service life.

It will be seen that the present invention attains the several objects and advantages summarized above, namely: Facilitates an interoperative determination of the appropriate neck length and head offset for a femoral component in a total hip arthroplasty; enables relatively quick and effective interoperative trialing for evaluation of hip mechanics at a prosthetic hip implant site; allows selective changes in distance and offset between the femoral stem and a trial femoral head of a femoral trial in a prosthetic hip joint for interoperatively determining an appropriate neck length and head offset in the femoral component of the prosthetic hip joint itself, without the necessity for serial replacements of the entire trial and concomitant multiple dislocations and reductions of the hip joint; allows such selective changes in distance and offset to be accomplished with a single apparatus, utilizing a single operator coupled readily to the apparatus and capable of operation from a location remote from the implant site; provides for the ready replication of any one of a plurality of predetermined combinations of neck length and head offset available in a given hip replacement system to enable selection of the combination most appropriate to a particular implant site; enables interoperative evaluation of hip mechanics at a hip implant site for consistent, precise results attained with ease and in less time; improves accuracy in the completion of a total hip arthroplasty; facilitates the conduct of minimally invasive total hip arthroplasty, where access to the hip joint is more limited; reduces pain and discomfort, as well as recovery time, in patients subjected to total hip arthroplasty.

It is to be understood that the above detailed description of preferred embodiments of the invention is provided by way of example only. Various details of design, construction and procedure may be modified without departing from the true spirit and scope of the invention, as set forth in the appended claims.

The embodiments of the invention in which an exclusive property or privilege is claimed are defined as follows:

1. Apparatus for interoperatively determining, during a trialing procedure conducted in connection with total hip arthroplasty at an implant site, a combination of neck length along a predetermined direction and femoral head offset required in a femoral component to be engaged with an acetabular component in a prosthetic hip joint to be implanted at the implant site for establishing appropriate hip mechanics in the prosthetic hip joint, by selecting a combination of trial distance, along a predetermined direction, and trial offset between a trial femoral head and a femoral stem component placed at the implant site with the trial femoral head engaged with an acetabular component in a trial hip joint, the combination of trial distance and trial offset corresponding to the combination of neck length and femoral head offset required in the prosthetic hip joint, the apparatus comprising:

a trial femoral head component including a trial femoral head having a center of rotation;

an indexing arrangement coupling the trial femoral head component with the femoral stem component for selective movement relative to one another, during the trialing procedure, the indexing arrangement being dimensioned and configured such that the selective relative movement includes longitudinal movement of the trial femoral head along a longitudinal axis extending essentially parallel with the predetermined direction and lateral movement of the trial femoral head relative to the longitudinal axis for establishing a trial hip joint having a selected combination of trial distance and trial offset between the trial femoral head and the femoral stem component;

the indexing arrangement including a drive shaft extending along a drive axis essentially parallel with the predetermined direction and journaled for rotation about the drive axis, and a coupling arrangement coupling the trial femoral head component with the drive shaft for movement of the trial femoral head component along the longitudinal axis and for rotation of the trial femoral head component about the longitudinal axis in response to rotation of the drive shaft about the drive axis, the center of rotation of the trial femoral head being offset laterally from the longitudinal axis, the coupling arrangement including a lead groove and a follower engaged with the lead groove, the lead groove following a modified helical path and including segments for advancing the trial femoral head component along the longitudinal axis, and for moving the center of rotation of the trial femoral head to offset the trial femoral head laterally in response to rotation of the drive shaft such that movement of the trial femoral head component is among selected positions corresponding to selectable combinations of trial distance and trial offset; and a drive mechanism dimensioned and configured for selectively driving the indexing arrangement to index the trial femoral head component among selected combinations of trial distance and trial offset, during interoperative trialing to evaluate hip mechanics in the trial hip joint, thereby determining interoperatively an appropriate combination of trial distance and trial offset, the appropriate combination of trial distance and trial offset corresponding to the combination of neck length and femoral head offset required in the femoral component for establishing the appropriate hip mechanics in the prosthetic hip joint.

2. The apparatus of claim 1 wherein the selected positions comprise predetermined selectable positions such that selection of a predetermined position determines the neck length and the femoral head offset required in the femoral component for establishing the appropriate hip mechanics in the prosthetic hip joint.

3. The apparatus of claim 1 including a trial proximal housing and wherein the lead groove is carried by the trial proximal housing and the follower is on the trail femoral head component.

4. The apparatus of claim 3 wherein the selected positions comprise predetermined selectable positions such that selection of a predetermined position determines the neck length and the femoral head offset required in the femoral component for establishing the appropriate hip mechanics in the prosthetic hip joint.

5. The apparatus of claim 4 including indicators for indicating placement of the trial femoral head component at corresponding selected predetermined positions.

6. The apparatus of claim 5 wherein the indicators comprise stops for holding the trial femoral head component at a corresponding selected predetermined position.

7. The apparatus of claim 4 including a number of segments, the number of segments providing combinations of trial distance and trial offset corresponding to combinations of neck length and femoral head offset available in a femoral component of selected size.

8. The apparatus of claim 7 wherein the combinations comprise six predetermined combinations corresponding to six combinations available in the femoral component of selected size.

* * * * *